United States Patent
Takahata et al.

(10) Patent No.: US 7,866,221 B2
(45) Date of Patent: Jan. 11, 2011

(54) METHOD FOR STORING PIPETTE CHIP

(75) Inventors: Kazuaki Takahata, Mitaka (JP); Tetsuo Okabe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 30 days.

(21) Appl. No.: 12/375,932

(22) PCT Filed: Aug. 6, 2007

(86) PCT No.: PCT/JP2007/065789
§ 371 (c)(1),
(2), (4) Date: Jan. 30, 2009

(87) PCT Pub. No.: WO2008/018606
PCT Pub. Date: Feb. 14, 2008

(65) Prior Publication Data
US 2009/0320621 A1    Dec. 31, 2009

(30) Foreign Application Priority Data
Aug. 9, 2006    (JP) .............................. 2006-216840

(51) Int. Cl.
*G01N 1/00* (2006.01)
(52) U.S. Cl. ................................. 73/864.25
(58) Field of Classification Search ............ None
See application file for complete search history.

(56) References Cited

U.S. PATENT DOCUMENTS 4,731,225 A    3/1988  Wakatake
2007/0003446 A1  1/2007  Takahata et al.
2009/0011413 A1  1/2009  Ishii et al.
2009/0137428 A1  5/2009  Okabe et al.

FOREIGN PATENT DOCUMENTS

| JP | 62-276466 A | 12/1987 |
|---|---|---|
| JP | 9-127128 A | 5/1997 |
| JP | 10-38897 A | 2/1998 |
| JP | 2003-294771 A | 10/2003 |
| JP | 2004-24981 A | 1/2004 |
| JP | 3569779 B2 | 9/2004 |
| JP | 2005-61957 A | 3/2005 |
| JP | 2007-139470 A | 6/2007 |

OTHER PUBLICATIONS

PCT International Search Report and Written Opinion of the International Searching Authority, Mailing Date Sep. 11, 2007.
U.S. Appl. No. 11/993,704, filed Jun. 29, 2006, Ishibashi, et al.

*Primary Examiner*—Robert R Raevis
(74) *Attorney, Agent, or Firm*—Fitzpatrick, Cella, Harper & Scinto

(57) ABSTRACT

A method for storing pipette chips for making a container for storing used pipette chips on a pipetting device compact is provided. A method for storing pipette chips including a step of moving a pipette chip to an entrance portion of a pipette chip container, a step of cutting at least a part of a pipette chip, a step of taking a cut pipette chip into the pipette chip container, and a step of stacking a pipette chip to be subsequently taken in onto a preceding taken-in pipette chip.

17 Claims, 3 Drawing Sheets

METHOD FOR STORING PIPETTE CHIP

TECHNICAL FIELD

The present invention relates to a method for storing a pipette chip in an device comprising a pipette using a pipette chip and in more particular, relates to a method for storing a used pipette chip in a compact manner and a constitution thereof.

BACKGROUND ART

In general, a pipetting device is known and is typically used in research institutes, hospitals and the like in order to suction and supply liquid in a predetermined quantity being a comparatively small quantity into a well of a plate such as a micro plate, a deep hole block and the like. Liquid supplied with a pipetting device is exemplified by blood and the other biological samples, solvents, reagents and the like. In order to omit troubles for cleaning a site where a pipetting device contact liquid to be suctioned, a mode of mounting a pipette chip is generally used. In that mode of device, a part or the whole of the above described liquid is generally taken out by suction of the pipetting device through the pipette chip from a set of plates or a liquid reservoir and is retained inside the pipette chip and subsequently supplied into the well of another plate.

In order to store a used pipette chip, a pipetting device on which a pipette chip is mounted, that is, an device adapted to comprise a waste container disposed separately from the rack of the pipette chip is widely used. In the device with that constitution, a used pipette chip is temporarily stored in a waste container which is collectively abandoned at a point of time when pipette chips are stored to some extent inside the waste container. At that occasion, the waste container is cleaned for preventing contamination and thereafter is used again or abandoned together with the used pipette chips.

On a waste container, Japanese Patent Application Laid-Open No. 2005-61957 discloses a waste box detachably attachable to a pipetting device and can be covered with a cover and the like for preventing pollution. In addition, Japanese Patent Application Laid-Open No. H09-127128 and Japanese Patent No. 03569779 disclose a chip cartridge accompanying a waste tray integrally comprising a cartridge portion in which a waste container for storing pipette chips after use and a plurality of pipette chips used for sampling solution can be arranged.

In addition, Japanese Patent Application Laid-Open No. H62-276466 discloses an automatic analyzer with a pipette.

DISCLOSURE OF THE INVENTION

An object of the present invention is to provide a method for storing pipette chips for making a storing container for storing used pipette chips on a pipetting device compact and a pipetting device practicing that storing method.

The present invention is directed to a method for storing a pipette chip comprising the steps of:

(a) cutting at least a part of a pipette chip, (b) stacking a plurality of cut pipette chips together more closely using a deformability of a pipette chip obtained by cutting, and (c) storing the cut pipette chip in a predetermined storage area. The stacking step and the storing step can be carried out concurrently.

The present invention is directed to a method for storing a pipette chip comprising the steps of:

(1) moving a pipette chip to an entrance portion of a pipette chip container, (2) cutting at least a part of the pipette chip, (3) taking in the pipette chip container a pipette chip obtained by the cutting from a nozzle tip end of the cut pipette chip, and (4) stacking another pipette chip subjected to the moving through taking steps on the pipette chip taken in inside the pipette chip container in the state that the subsequently stored pipette chip is inserted into the previously stored pipette chip.

The present invention is directed to a pipetting device comprising:

a head including a pipette to and from which a pipette chip can be attached and removed, a head-moving unit for moving the head, a pipette chip container, a unit for cutting at least a part of the pipette chip, a unit for storing a pipette chip obtained by the cutting in the pipette chip container, and a unit for stacking the cut pipette chips together more closely using a deformability of the cut pipette chip.

The present invention is directed to a pipetting device including:

a head including a pipette to and from which a pipette chip can be attached and removed, a head-moving unit for moving the head, and a pipette chip container, the pipette chip container having a storage entrance for taking in the pipette chip container a pipette chip from a nozzle end of the pipette chip, a cutting portion for cutting the pipette chip and a storage portion for stacking and storing the pipette chip onto a previously stored pipette chip, a passage being formed by connecting the storage entrance, the cutting portion and the storage portion in series to make the pipette chip retain a state with the nozzle end as a tip end and movable.

The movement of the head can bring a pipette chip mounted on the pipette to an entrance portion of the pipette chip container.

The movement of the head can press a pipette chip mounted on the pipette against the cutting portion to carry out the cutting.

The movement of the head can cause the pipette to push a pipette chip taken in the pipette chip container in a pipette chip previously taken in the pipette chip container to enable the pipette chips to be stacked.

The pipette chip container can include a unit for fixing a pipette chip first taken in the pipette chip container.

In the pipetting device, a partition can be provided inside the pipette chip container to form a storage portion partitioned equal to the number of the storage entrances with an width which allows pipette chips taken in the pipette chip container with a nozzle end down and a mounting opening up to be held without falling down and to be stacked.

The storage entrance provided to the pipette chip container can be narrower than the width of the storage portion.

The present invention is directed to a pipette chip container used for a pipetting device including a head including a pipette to and from which a pipette chip can be attached and detached, and a head-moving unit for moving the head, the pipette chip container having a storage entrance for taking in the pipette chip container a pipette chip from a nozzle end of the pipette chip, a cutting portion for cutting the pipette chip and a storage portion for stacking and storing the pipette chip onto a previously stored pipette chip and a passage being formed by connecting the storage entrance, the cutting portion and the storage portion in series to make the pipette chip retain a state with the nozzle end as a tip end retain movable.

In the pipette chip container, a movement of the head can cause the cutting portion to press a pipette chip mounted on the pipette against the cutting portion to carry out the cutting.

In the pipette chip container, a movement of the head can cause the pipette to push a pipette chip taken in the pipette chip container in a pipette chip previously taken in the pipette chip container to enable the pipette chips to be stacked.

The pipette chip container can include a unit for fixing a pipette chip first taken in the pipette chip container.

In the pipette chip container, a partition can be provided inside the pipette chip container to form a storage portion partitioned equal to the number of the storage entrances with width which allows pipette chips taken in the pipette chip container with a nozzle end down and a mounting opening up to be held without falling down and to be stacked.

The storage entrance provided to the pipette chip container can be narrower than partitioned width of the storage portion.

The present invention is directed to a biochemical examination device characterized by including:

a reaction unit allowing installation of a reaction container, an installation stand for a reagent container including a plurality of concave portions housing a reagent for treating a sample, and the above pipetting device.

The sample can include at least one kind selected from the group consisting of nucleic fragments, DNA, oligonucleotide or protein and is utilized for genetic testing.

The present invention can make a container storing pipette chips after use in a pipetting device compact. In addition, in the case of a pipette chip container of a determined size, more pipette chips can be stored.

Further features of the present invention will become apparent from the following description of exemplary embodiments with reference to the attached drawings.

BRIEF DESCRIPTION OF THE DRAWINGS

FIG. 8A illustrates a state prior to removal and FIG. 8B illustrates a state at removal.

BEST MODE FOR CARRYING OUT THE INVENTION

Figure 1:
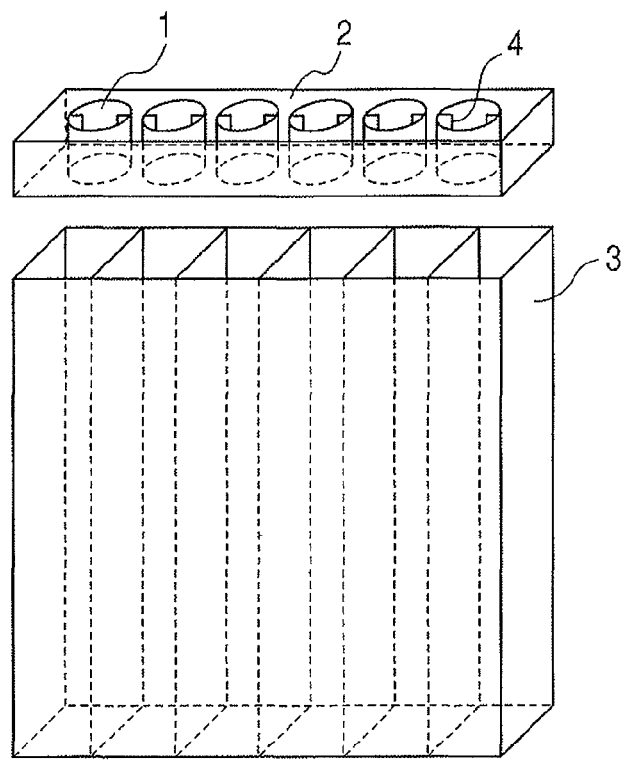
FIG. 1 is a perspective view describing structure of a pipette chip storing container related to an embodiment of the present invention.

A method for storing a pipette chip of the present invention includes the following steps:

(a) a step of cutting at least a part of a pipette chip.

(b) a step of stacking a plurality of cut pipette chips together more closely using deformability of the pipette chip obtained by cutting.

(c) a step of storing the cut pipette chip in a predetermined storage area.

In the step (a), a region where the pipette chip is cut is a side plane of the pipette chip and at least the periphery portion of the pipette mounting opening end needs to be included. In addition, desirably the pipette chip is cut in the longitudinal direction (flow path direction of the pipette chip). The whole side plane of the pipette chip is desired to be the cutting region for the step (a). However if at least a part is cut, it will do. A reason thereof is that a step of stacking together is followed by further tearing of an outside pipette chip stacked together and finally cutting the side plane over the entire length. In addition, not only a plurality of but also a single cutting site will not give rise to any problem. Cutting apart like that will enable deformation on a chip side plane. The cut-off pipette chip side plane can be spread toward outside and extended as well. By repeating, on a plurality of cut pipette chips, the method of opening a chip side plane outward and stacking another pipette chip together inside, a plurality of pipette chips can be stacked together. Such stacking together enables increase in the number of storable pipette chips per unit volume and enables integrated storage. Here, the order of the step (b) and the step (c) can be rearranged. That is, a plurality of cut pipette chips can be stacked together and thereafter stored in a predetermined storage region. The pipette chip may be stacked together after having been stored in the storage region. Moreover, one desirable embodiment can carry out the step (b) and the step (c) concurrently. In addition, the storage region is a region for retaining the stored pipette chips. For example, a pipette chip container equal to a pipette chip in height or higher than the length of the pipette chip and including a storage entrance to become a leading portion can be suitably used as a storage region.

A pipetting device using a method for storing a pipette chip is adapted to include:

a head including a pipette to and from which a pipette chip can be attached and removed, a head-moving unit for moving a head, a pipette chip container, a unit for cutting a part of a pipette chip, a unit for storing a cut pipette chip in the pipette chip container, and a unit for stacking a plurality of cut pipette chips together more closely using deformability of the pipette chip obtained by cutting.

In one embodiment, in operations of a head-moving unit, a pipette chip mounted on a pipette can be pushed against a pipette chip cutting unit and can be stored in a pipette chip container or a plurality of cut pipette chips can be closely stacked together.

An embodiment of a storage method of the present invention includes the following steps.

(1) A step of moving a pipette chip to an entrance portion of a pipette chip container.

(2) A step of cutting at least a part of a pipette chip.

(3) A step of taking a cut pipette chip into the pipette chip container.

(4) a step of stacking another pipette chip subjected to the steps (1) to (3) on the pipette chip taken in inside the pipette chip container in the state where the subsequently stored pipette chip is inserted into the previously stored pipette chip. Here, the region where a pipette chip is cut is desirably the entire side plane of a pipette chip. However if at least a part is cut, it will do. A reason thereof is that the cut plane of a chip on the side to be stacked spreads (tears) by being pushed by stacking chips at an occasion of stacking together and repetition hereof enables storage in the entirely cut state at last. If the entire side plane of a chip on the stacked side is cut, the chip to be stacked can be stacked to reach the pipette mounting opening of the chip on the side to be stacked. In that case, the stacked height will be approximately the same as the height of a pipette chip and the approximate width of the pile will be derived by chip outer diameter+chip thickness×(number of piles−1). Thus, in order to cut the entire side plane of a pipette chip which is stacked in a pipette chip container, the side plane of a pipette chip including the periphery at an end of the pipette mounting opening is desirably cut by one third or more of the entire length of the pipette chip in the longitudinal direction.

In the step (3), in the case of taking in a pipette chip into the pipette chip container in a posture with a nozzle end (tip portion) of a pipette chip being disposed downward and an end portion of a mounting opening side to a pipette (base end portion) being disposed above, the pipette chip is desirably stored so as not to fall down or not to tilt. For that purpose, at least horizontal movements are desirably restricted. In addition, fixation of a pipette chip at a position where it is originally stored at first in the pipette chip container is desirable for pushing a pipette chip to be stacked afterwards into the previously stored pipette chip.

Figure 8A:
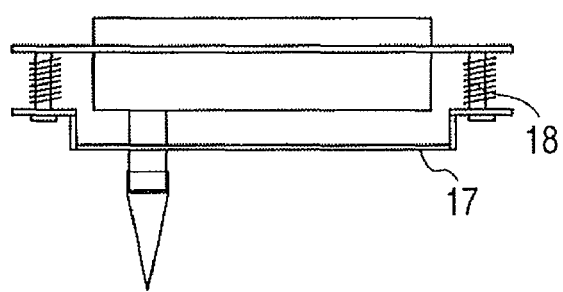
FIGS. 8A and 8B are diagrams illustrating an example of a mechanism for removing pipette chips related to an embodiment of the present invention from a pipette.
Figure 8B:
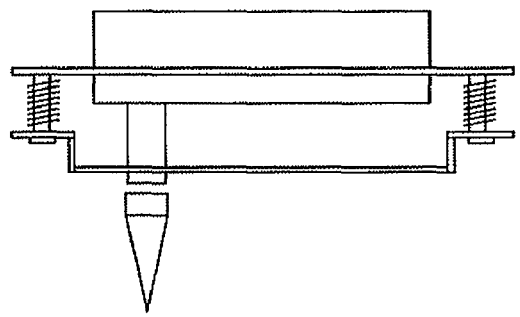

The storage method of the present invention can be suitably carried out in a pipetting device as adapted below. That is, a pipetting device includes a head including a pipette to and from which a pipette chip can be attached and removed, a head-moving unit for moving that head, a cutting portion for cutting a pipette chip, and a pipette chip container for storing a cut pipette chip. With that device, in the step (1) of the storage method of the present invention, head movement with a head-moving unit enables the pipette chip mounted on the pipette provided in the head to move to the entrance portion of the pipette chip container. As for the step (2) of the storage method, in the case where the pipette chip container comprises a cutting portion, for example, the head-moving unit moves the head to push the pipette chip to the cutting portion provided in the pipette chip container and thereby the pipette chip can be cut. Otherwise, besides the head-moving unit, the pipetting device can include a pushing unit for pushing a pipette chip to the cutting portion and thereby push the pipette chip to the cutting portion to cut the pipette chip. Moreover, as a separate cutting method, the pipette chip is stored in the pipette chip container subjected to removal and thereafter the cutting portion can be pushed to the pipette chip and cut. The cut pipette chip is occasionally removed from a pipette automatically. However, the pipetting device includes a pipette chip removing unit for removing a pipette chip and the pipette chip can be removed thereby. A mechanism comprising a remover 17 as a removing unit as illustrated in FIGS. 8A and 8B, for example, is mounted on a pipetting device body. A pipette ascends and thereby to push the pipette chip downward to enable removal. In the case of adopting the pipette chip container to be described below, that removal can be carried out after the pipette chip is cut at the storage entrance and is pushed in the interior of the storage portion.

Moreover, as for the step (4) of the storage method of the present invention, the head movement can push the pipette chip taken in the interior of the pipette chip container to the previously taken-in pipette chip and pile them through a pipette.

In addition, the pipetting device can include a pipette chip rack for installing an unused pipette chip.

The pipette chip container arranged in the above described pipetting device is suitably adapted to form a pipette chip passage by connecting a storage entrance for taking in a pipette chip, a cutting portion for cutting a pipette chip and a pipette chip container for stacking and storing pipette chips in series.

That passage is formed to provide movable area by maintaining the state where the pipette chip takes the nozzle end thereof as the top and thereby a predetermined portion of the pipette chip will be possibly brought into contact to the cutting portion. In addition, insertion of a cut pipette chip to be subsequently stored lead by a nozzle end thereof into the mounting opening of a previously stored pipette chip which is already cut will become feasible. Moreover, that passage is formed to shape a straight pipe and the inner wall plane thereof is structured to allow restriction on the position of the side plane of the pipette chip to form the pipette chip movement route to shape approximately a straight line. Thereby, effective cutting and stacking will become feasible and compactness of the pipette chip container can be attained.

Here, the cutting portion is desirably adapted to include the periphery of the pipette mounting opening end of the pipette chip to cut it in the longitudinal direction.

In the case where the storage portion is provided cylindrically to extend in the vertical direction, the storage portion desirably retains the pipette chip with the tip portion of a pipette chip disposed downward and the base portion disposed upward without falling it down and has an area in the horizontal direction enabling stacking and storage of the pipette chip. For example, a straight-piped passage is formed by connecting the storage portion, which is made cylindrical, to the storage entrance provided with a cutting blade and the section of that passage is made slightly larger than the section of the portion of the pipette chip with the maximum outer diameter. Thereby restriction on the position of the above described pipette chip inside the passage will become easier. For example, a section of the portion of the pipette chip with the maximum outer diameter and the storage portion can be set to provide a gap of 10 mm to 20 mm.

The shape of the intersecting (for example, perpendicularly intersecting) section in the axial direction in the case where the storage portion is formed to shape a cylinder can be polygonal, that is, triangular, quadrangular, pentagonal, hexagonal and the like, circular, oval and the like.

The storage entrance can include a shape making storage of the pipette chip easier and is desirably circular with a diameter larger than the maximum outer diameter of the pipette chip. In that case, for example, the gap between the portion of the pipette chip with the maximum outer diameter and the storage entrance can be set within the range of 1 mm to 10 mm. In addition, the storage office is desirably narrower than the storage portion. In the case where the storage entrance is circular, the storage entrance can be set smaller than the section perpendicular to the movement direction of the pipette chip in the storage portion. For example, in the case where the storage portion is a cylindrical square in section, the diameter of the storage entrance is made slightly smaller than length of one side of the square of the storage portion in section. In addition, with the section being rectangular, the diameter of the storage entrance is made smaller than length of the shorter side. Thus, by making the diameter of the storage entrance smaller than the partition width of the storage portion, the diameter of the pipette chip stacked inside the storage portion expands to get larger than the storage entrance. Thereby the chip can be prevented from getting out of the container.

In the case of including a plurality of storage entrances, each storage entrance is desirably provided in structure with a storage portion with such an area allowing stacking without falling down as many as the storage portion in number by partitions.

In addition, the pipette chip container is adapted to include the freely openable bottom portion and can be a mode to take out the pipette chips stacked inside the storage portion from the storage portion at a stage where the storage portion is fulfilled so that the pipette chip container is reused. In the case of adopting such a constitution, in order to prevent contamination, a periodical cleaning, sterilization and the like are desirably carried out.

Moreover, the present invention includes a biochemical examination device comprising a pipetting device including the constitution as described above. That is, a biochemical examination device of the present invention is adapted to include a reaction unit allowing installation of a reaction container, an installation stand for a reagent container including a plurality of concave portions housing a reagent for treating a sample, and a pipetting device with the above described constitution. That biochemical examination device can further include an installation stand for installing a sample container housing a solution including a sample. The biochemical examination device hereof is suitably utilized for genetic testing with a sample including at least one kind selected from the group consisting of nucleic fragments, DNA, oligonucleotide or protein.

A general shape of a pipette chip is a longitudinal hollow tubular body including a base end portion and a tip end portion, the base end portion including a mounting opening onto a pipette and the tip end portion including an opening for suctioning and discharging liquid. The hollow tubular body of the pipette chip is adapted to include, for example, a cylinder, a cone and a part thereof, and moreover, a tubular body shaped to include a longitudinal section inclined toward the centripetal direction in a curved manner and the diameter thereof gets smaller in the direction from the base end portion to the tip end portion. To a pipette chip in such a general shape, the storage method of the present invention is applicable. Therefore a pipette chip on the market is applicable without problems.

In addition, for a general pipette chip with PP (polypropylene) as material, the storage method of the present invention is suitably used. However, the one having undergone coating treatment with silicon and another material give rise to no problem as well. Moreover, to a chip with a filter, the method of the present invention is applicable.

In the case of inserting the tip end portion of one pipette chip to the mounting opening of the other pipette chip to form a stacked state, insertion can go on until the two pipette chips are brought into contact on the circumference making the inner diameter of the mounting opening of the preceding pipette chip the same as the diameter of the outside side plane of the latter pipette chip in size. Depending on thickness and the like of the side plane of the pipette chip, a cylindrical shape in the base end portion of the pipette chip, for example, is larger than a conical shape in non-stacked region and therefore, cutting in the storage method of the present invention will become effective. Accordingly, the storage method of the present invention can be utilized to a pipette chip with any shape without any particular limitation but, in particular, can be suitably utilized to a pipette chip shaped to include a lot of cylindrical portion.

EMBODIMENTS

Embodiments related to the present invention will be described based on the drawings as follows.

Embodiment 1

FIG. 1 is a perspective view describing structure of a container related to an embodiment of the present invention. A pipette chip container is adapted to include a storage entrance plate (2) provided with a storage entrance (1) for storing a pipette chip into a container and a storage portion (3) for stacking pipette chips to store the pipette chips. The inner side of the storage entrance (1) is provided with a cutting portion (4) comprising a plurality of blades protruding toward inside a passage of the pipette chip to cut the pipette chip. The storage entrance plate (2) is removable from the storage portion (3). The interior of the storage portion (3) is partitioned by partition walls to form sections in the same number as the number of the storage entrance (1) with an area allowing pipette chips to be stacked without falling down and stored. In addition, height of the pipette chip container (16) is designed lower than the height of the position of the pipette chip tip mounted on a pipette at an occasion when the pipette chip container moves to the storage entrance.

Figure 2:
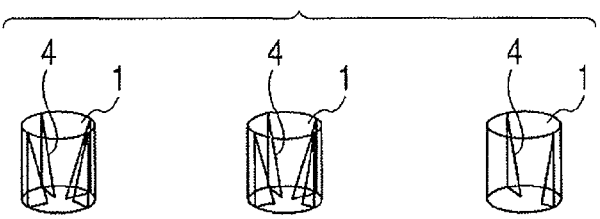
FIG. 2 is a perspective view of a storage entrance and a cut portion related to an embodiment of the present invention.
Figure 3:
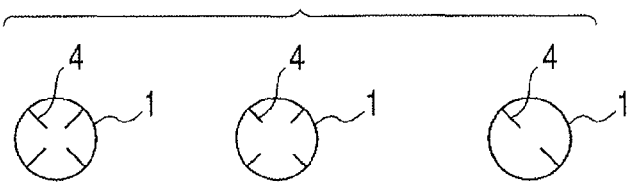
FIG. 3 is a top view of storage entrances and cutting portions related to an embodiment of the present invention.

FIG. 2 is a perspective view of a storage entrance and a cut portion of a container related to an embodiment of the present invention. FIG. 3 is a top view of storage entrances and cutting portions. The present embodiment presents three types of the cutting portion (4) inside the storage entrance (1), one cutting portion comprising long four blades, another cutting portion comprising four blades with half length and still another cutting portion comprising two blades with half length.

The above described pipette chip container cuts pipette chips and stacks to enable compact storage of used pipette chips. In addition, on the pipetting device, compactness of the pipette chip container for the used pipette chips is attainable.

Embodiment 2

Figure 4:
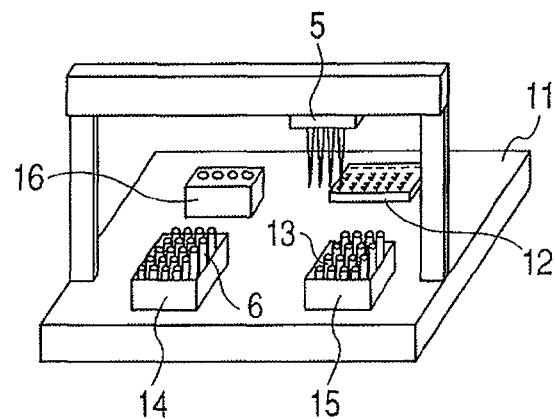
FIG. 4 is a perspective view describing a unit for stacking and storing pipette chips related to an embodiment of the present invention.
Figure 5:
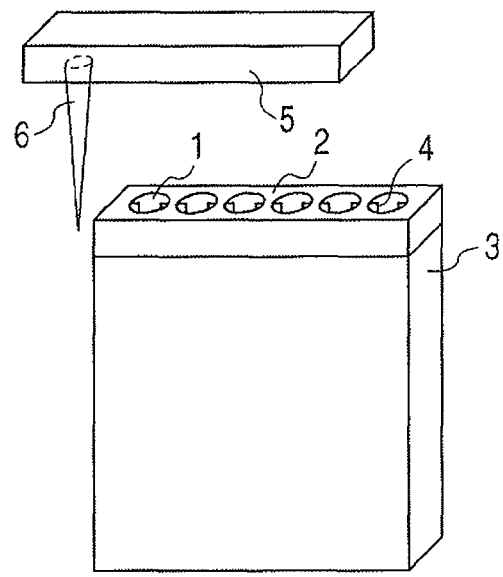
FIG. 5 is a diagram illustrating a unit for moving a pipette chip related to an embodiment of the present invention to a container for storage.
Figure 6:
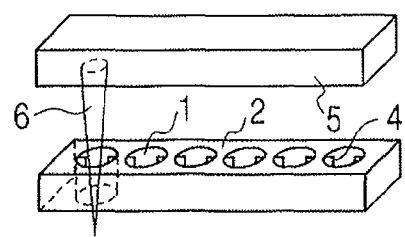
FIG. 6 is a diagram illustrating a unit for cutting a pipette chip related to an embodiment of the present invention.
Figure 7:
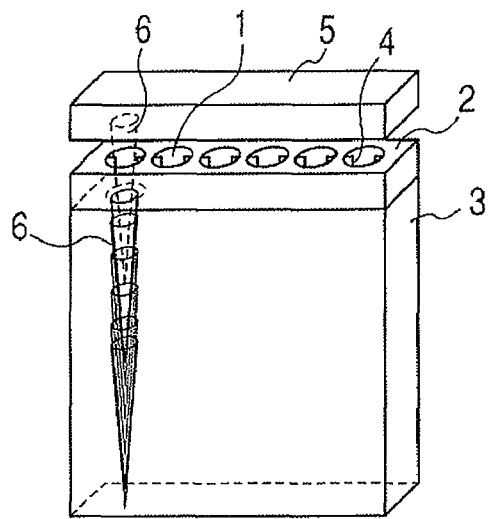
FIG. 7 is a diagram illustrating a unit for stacking pipette chips related to an embodiment of the present invention.

FIG. 4 is a perspective view describing a unit for stacking and storing pipette chips related to an embodiment of the present invention. Corresponding with the application of the pipetting device, there are a lot of variations such as the case of dispensing from a micro tube to a micro tube or to a well plate, the case of dispensing one sample to a plurality of containers (micro tubes, well plates and the like) and the like. Here, an device for dispensing a sample solution included in a micro tube into a well plate will be exemplified for description. The pipette (5) is moved to a pipette chip (6) installed in a pipette chip rack (14). The pipette (5) is caused to descend so that the pipette chip (6) is mounted thereon. In that case, the pipette (5) is movable along an X axis, a Y axis and a Z axis with a mechanism not illustrated in the drawing. In addition, the sample solution can be suctioned or discharged with a mechanism not illustrated in the drawing. The pipette (5) is caused to ascend to move the pipette (5), on which the pipette chip (6) is mounted, to a micro tube (13) installed in a micro tube installation container. The pipette (5) is caused to descend to suction the sample solution included in the micro tube. The pipette (5) is caused to ascend to move to the well plate (12). The pipette (5) is caused to descend to discharge the sample solution of the pipette chip (6) into the well plate. The pipette (5) is caused to ascend to move to the storage entrance (1) of the pipette chip container (16) for disposing the pipette chip (6) (FIG. 5). The pipette (5) is caused to descend to cut the pipette chip (6) with a cutting portion (4) provided in the storage entrance (1) (FIG. 6). The pipette (5) is caused to descend further to remove the cut pipette chip (6) and store it in the pipette chip container (16). The cut pipette chip (6) is fixed and retained inside the waste container (16). At that occasion, the inner diameter of the storage entrance of the container storing the pipette chip is desirably smaller than a section in the horizontal direction of the container portion storing the pipette chip. For example, in the case where the section as illustrated in FIG. 1 in the horizontal direction is rectangular, the diameter of the storage entrance is set to be shorter than the shorter side (partition width) of that rectangular. By setting that way, the stored pipette chip can be fixed to a state where the storage portion and the partition wall can stack the subsequent pipette chip.

In the case of stacking and storing pipette chips, after cutting the reused pipette chip (6) with the cutting portion (4) provided in the storage entrance (1), the pipette (5) is caused to descend further to store the pipette (5) into the container (16). As described above, the cut pipette chip is stacked inside the container (16). The cut pipette chip (6) is removed and the pipette (5) is caused to ascend. In the case of repeating dispensing, the pipette (5) is moved again to the pipette chip (6) installed in the pipette chip rack (14).

As described above, in the case of repeatedly dispensing the sample solution included in the micro tube to the well plate, the used pipette chips are stacked in a container and thereby enable compact storage so that the pipette chip container can be made small on a pipetting device.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2006-216840 filed on Aug. 9, 2006, which is hereby incorporated by reference herein.

The invention claimed is:

1. A method for storing a pipette chip comprising the steps of:
   (a) cutting at least a part of a pipette chip;
   (b) stacking a plurality of cut pipette chips together more closely using a deformability of a pipette chip obtained by cutting; and
   (c) storing the cut pipette chip in a predetermined storage area.

2. The method for storing a pipette chip according to claim 1, wherein the stacking step and the storing step are carried out concurrently.

3. A method for storing a pipette chip comprising the steps of:
   (1) moving a pipette chip to an entrance portion of a pipette chip container;
   (2) cutting at least a part of the pipette chip;
   (3) taking into the pipette chip container a pipette chip obtained by the cutting from a nozzle tip end of the cut pipette chip; and
   (4) stacking another pipette chip subjected to the steps (1) to (3) onto the pipette chip taken in inside the pipette chip container, in the state that the subsequently stored pipette chip is inserted into the previously stored pipette chip.

4. A pipetting device comprising:
   a head including a pipette to and from which a pipette chip can be attached and removed;
   a head-moving unit for moving the head; and
   a pipette chip container comprising:
   a unit for cutting at least a part of the pipette chip;
   a unit for storing a pipette chip obtained by the cutting in the pipette chip container; and
   a unit for stacking cut pipette chips together more closely using a deformability of the cut pipette chip.

5. A pipetting device comprising:
   a head including a pipette to and from which a pipette chip can be attached and removed;
   a head-moving unit for moving the head; and
   a pipette chip container,
   wherein the pipette chip container has a storage entrance for taking into the pipette chip container a pipette chip from a nozzle end of the pipette chip, a cutting portion for cutting the pipette chip, and a storage portion for storing the pipette chip by stacking onto a previously stored pipette chip, and
   wherein a passage is formed inside the container by connecting the storage entrance, the cutting portion and the storage portion in series to make the pipette chip retain the nozzle end as a tip end while moving within the passage.

6. The pipetting device according to claim 5, wherein the movement of the head brings a pipette chip mounted on the pipette to the storage entrance of the pipette chip container.

7. The pipetting device according to claim 5, wherein the movement of the head presses a pipette chip mounted on the pipette against the cutting portion to carry out the cutting.

8. The pipetting device according to claim 5, wherein the movement of the head causes the pipette to push a pipette chip taken into the pipette chip container into a pipette chip previously taken into the pipette chip container to enable the pipette chips to be stacked.

9. The pipetting device according to claim 5, wherein the pipette chip container includes a unit for fixing a pipette chip first taken into the pipette chip container.

10. The pipetting device according to claim 5, wherein a partition is provided inside the pipette chip container to form a storage portion partitioned equal to the number of the storage entrances, with a width which allows pipette chips to be taken into the pipette chip container being held with a nozzle end down and a mounting opening up without falling down and being stacked to be stored.

11. The pipetting device according to claim 10, wherein the storage entrance provided to the pipette chip container is narrower than the width of the storage portion.

12. A pipette chip container used for a pipetting device, the pipetting device comprising:
   a head including a pipette to and from which a pipette chip can be attached and detached; and
   a head-moving unit for moving the head,
   wherein the pipette chip container has a storage entrance for taking into the pipette chip container a pipette chip from a nozzle end of the pipette chip, a cutting portion for cutting the pipette chip, and a storage portion for stacking and storing the pipette chip onto a previously stored pipette chip, and
   wherein a passage is formed inside the container by connecting the storage entrance, the cutting portion and the storage portion in series to make the pipette chip retain the nozzle end as a tip end while moving within the passage.

13. The pipette chip container according to claim 12, wherein a movement of the head causes the cutting portion to press a pipette chip mounted on the pipette against the cutting portion to carry out the cutting.

14. The pipette chip container according to claim 12, wherein a movement of the head causes the pipette to push a pipette chip taken into the pipette chip container into a pipette chip previously taken into the pipette chip container to enable the pipette chips to be stacked.

15. The pipette chip container according to claim 12, wherein the pipette chip container includes a unit for fixing a pipette chip first taken into the pipette chip container.

16. The pipette chip container according to claim 12, wherein a partition is provided inside the pipette chip container to form a storage portion partitioned equal to the number of the storage entrances, with a width which allows pipette chips to be taken into the pipette chip container with a nozzle end down and a mounting opening up without falling down and being stacked to be stored.

17. The pipette chip container according to claim 16, wherein the storage entrance provided to the pipette chip container is narrower than the partitioned width of the storage portion.

* * * * *